(12) United States Patent

Yeh et al.

(10) Patent No.: US 12,576,257 B2

(45) Date of Patent: Mar. 17, 2026

(54) TAMPER-RESISTANT CAP

(71) Applicant: CareFusion 303, Inc., San Diego, CA (US)

(72) Inventors: Jonathan Yeh, Diamond Bar, CA (US); Marco Cheng, Tustin, CA (US)

(73) Assignee: CAREFUSION 303, INC., San Diego, CA (US)

( * ) Notice: Subject to any disclaimer, the term of this patent is extended or adjusted under 35 U.S.C. 154(b) by 118 days.

(21) Appl. No.: 18/486,597

(22) Filed: Oct. 13, 2023

(65) Prior Publication Data

US 2024/0033496 A1 Feb. 1, 2024

Related U.S. Application Data

(63) Continuation of application No. 17/018,882, filed on Sep. 11, 2020, now Pat. No. 11,819,652, which is a (Continued)

(51) Int. Cl.
*A61M 39/20* (2006.01)
*A61M 5/50* (2006.01)

(Continued)

(52) U.S. Cl.
CPC ........ *A61M 39/1011* (2013.01); *A61M 39/20* (2013.01); *A61J 1/1412* (2013.01);

(Continued)

(58) Field of Classification Search
CPC .... A61M 5/3202; A61M 5/50; A61M 5/5096; A61M 39/1011; A61M 39/20;

(Continued)

(56) References Cited

U.S. PATENT DOCUMENTS

| | | | | |
|---|---|---|---|---|
| 662,812 A | * | 11/1900 | Perry | B65D 45/322 |
| | | | | 215/272 |
| 1,441,742 A | * | 1/1923 | O'Brien | B65D 45/322 |
| | | | | 215/272 |

(Continued)

FOREIGN PATENT DOCUMENTS

| | | |
|---|---|---|
| CN | 1258543 A | 7/2000 |
| CN | 1210074 | 7/2005 |

(Continued)

OTHER PUBLICATIONS

Japanese Office Action for Application No. 2023-142651, dated Jun. 5, 2024, 4 pages including translation.

(Continued)

*Primary Examiner* — Gideon R Weinerth

(74) *Attorney, Agent, or Firm* — MASCHOFF BRENNAN

(57) ABSTRACT

A cap for coupling to a medical adapter may include a housing with a closed top end and an open bottom end with legs that extend from the housing away from the bottom end. Members may extend from an inner surface of the legs to engage and secure the cap to a medical adapter or an insert configured to mate with a medical adapter. A cap may include angular ridges between a cap housing and an insert to permit rotation of the cap in single direction and prevent removal of the cap from a medical adapter. A cap may include hinged legs to permit the cap to be secured to a medical adapter by rotating the legs toward each other until a portion of a collar on each leg may be matingly joined around the medical adapter.

7 Claims, 12 Drawing Sheets

Related U.S. Application Data continuation of application No. 16/053,572, filed on Aug. 2, 2018, now Pat. No. 10,773,068, which is a continuation of application No. 14/814,302, filed on Jul. 30, 2015, now Pat. No. 10,039,913.

(51) Int. Cl.

| | |
|---|---|
| *A61M 39/10* | (2006.01) |
| *B65D 50/00* | (2006.01) |
| *B65D 51/00* | (2006.01) |
| *A61J 1/14* | (2023.01) |
| *A61M 5/32* | (2006.01) |
| *B65D 41/16* | (2006.01) |

(52) U.S. Cl.
CPC ............. *A61M 5/3202* (2013.01); *A61M 5/50* (2013.01); *A61M 5/5086* (2013.01); *B65D 41/16* (2013.01); *B65D 51/002* (2013.01)

(58) Field of Classification Search
CPC .... A61M 5/5086; A61J 1/1412; A61J 1/1425; B65D 41/16; B65D 43/0204; B65D 51/002; B65D 2401/30; B65D 2401/50
USPC ......... 206/438, 807; 215/250; 220/214, 319, 220/724; 604/111, 404, 192, 263; D24/130, 127
See application file for complete search history.

(56) References Cited

U.S. PATENT DOCUMENTS

| | | | | |
|---|---|---|---|---|
| 1,970,631 | A | * | 8/1934 | Sherman ................ B65D 41/04 |
| | | | | 222/551 |
| 2,013,527 | A | * | 9/1935 | Sherman ................ B65D 41/17 |
| | | | | 220/294 |
| 2,458,002 | A | * | 1/1949 | Kaskouras ............ E05B 13/001 |
| | | | | 70/2 |
| 2,816,550 | A | | 12/1957 | Hudson |
| 2,987,206 | A | * | 6/1961 | Grussen ................ B65D 41/485 |
| | | | | 215/250 |
| 3,104,681 | A | | 9/1963 | Gray, Jr. |
| 3,245,567 | A | | 4/1966 | Knight |
| 3,797,688 | A | | 3/1974 | Porcelli |
| 4,008,820 | A | | 2/1977 | Ruetz |
| 4,176,756 | A | * | 12/1979 | Gellman ............. B65D 51/002 |
| | | | | 403/309 |
| 4,202,378 | A | | 5/1980 | Bush |
| 4,241,188 | A | * | 12/1980 | Materia ................. C12M 29/20 |
| | | | | 435/317.1 |
| 4,286,640 | A | * | 9/1981 | Knox .................... A61J 1/1425 |
| | | | | 604/404 |
| 4,451,069 | A | | 5/1984 | Melone |
| 4,457,445 | A | * | 7/1984 | Hanks ................... G09F 3/0323 |
| | | | | 222/153.07 |
| 4,576,315 | A | | 3/1986 | Vitale |
| 4,631,056 | A | * | 12/1986 | Dye ................... A61M 39/1011 |
| | | | | 604/905 |
| 4,662,542 | A | | 5/1987 | Vitale |
| 4,664,259 | A | * | 5/1987 | Landis ................ A61M 5/3216 |
| | | | | 206/370 |
| 4,671,408 | A | * | 6/1987 | Raines ................. A61M 5/002 |
| | | | | 206/45.23 |
| 4,759,756 | A | | 7/1988 | Forman |
| 4,889,256 | A | | 12/1989 | Fowles |
| 4,921,096 | A | * | 5/1990 | McFarlane ......... A61M 25/002 |
| | | | | 206/349 |
| D311,868 | S | | 11/1990 | Armstrong |
| 5,040,694 | A | | 8/1991 | Gambello |
| 5,061,248 | A | | 10/1991 | Sacco |
| 5,084,032 | A | | 1/1992 | Kornberg |
| 5,104,379 | A | * | 4/1992 | Nakamura ......... B65D 55/0863 |
| | | | | 604/905 |
| 5,147,319 | A | | 9/1992 | Ishikawa |
| D337,310 | S | | 7/1993 | Yamaguchi |
| 5,279,576 | A | | 1/1994 | Loo et al. |
| 5,312,368 | A | * | 5/1994 | Haynes ............... A61M 5/3216 |
| | | | | 604/263 |
| 5,356,396 | A | | 10/1994 | Wyatt et al. |
| 5,360,404 | A | | 11/1994 | Novacek |
| 5,385,373 | A | * | 1/1995 | Love .................... F16B 41/007 |
| | | | | 403/313 |
| 5,458,580 | A | | 10/1995 | Haiishoreh |
| 5,531,695 | A | * | 7/1996 | Swisher ............. A61M 39/1011 |
| | | | | 604/905 |
| 5,591,134 | A | | 1/1997 | Shu |
| 5,626,371 | A | | 5/1997 | Bartholomew |
| 5,658,260 | A | | 8/1997 | Desecki |
| D393,722 | S | * | 4/1998 | Fangrow, Jr. ................ D24/129 |
| 5,893,480 | A | | 4/1999 | Dore |
| 5,925,032 | A | | 7/1999 | Clements |
| 6,085,920 | A | | 7/2000 | Moretti |
| 6,193,688 | B1 | | 2/2001 | Balestracci |
| 6,235,005 | B1 | | 5/2001 | Chang |
| 6,261,270 | B1 | | 7/2001 | Gault |
| D446,118 | S | | 8/2001 | Michael |
| 6,357,589 | B2 | * | 3/2002 | Schmidt ................. B65D 25/10 |
| | | | | 206/439 |
| 6,402,204 | B1 | | 6/2002 | Stuart |
| 6,409,705 | B1 | | 6/2002 | Kondo |
| 6,543,814 | B2 | | 4/2003 | Bartholomew |
| D495,416 | S | | 8/2004 | Dimeo et al. |
| 7,125,396 | B2 | | 10/2006 | Leinsing et al. |
| D616,984 | S | | 6/2010 | Gilboa |
| 7,867,215 | B2 | | 1/2011 | Akerlund |
| D637,713 | S | | 5/2011 | Nord et al. |
| 8,029,747 | B2 | | 10/2011 | Helmerson |
| D651,309 | S | * | 12/2011 | Rowe ........................... D24/130 |
| 8,091,727 | B2 | | 1/2012 | Domkowski |
| D655,017 | S | | 2/2012 | Mosler |
| D669,980 | S | | 10/2012 | Lev |
| D681,230 | S | | 4/2013 | Mosler |
| 8,512,295 | B2 | | 8/2013 | Shemesh |
| 8,512,309 | B2 | | 8/2013 | Shemesh et al. |
| 8,597,237 | B2 | | 12/2013 | Yow et al. |
| 8,753,325 | B2 | | 6/2014 | Lev |
| 8,771,045 | B2 | | 7/2014 | Geenen |
| 8,777,032 | B2 | | 7/2014 | Biesecker |
| 8,991,436 | B2 | | 3/2015 | Birch |
| 9,144,646 | B2 | | 9/2015 | Barron, III |
| 9,220,660 | B2 | | 12/2015 | Sund et al. |
| 9,339,438 | B2 | | 5/2016 | Lev |
| 9,352,348 | B2 | * | 5/2016 | Greiner-Perth ... A61M 15/0001 |
| 9,492,353 | B2 | | 11/2016 | Nord |
| 9,494,264 | B2 | * | 11/2016 | Avery ................... A61J 1/1418 |
| 9,532,926 | B2 | | 1/2017 | Whelan |
| 9,642,775 | B2 | | 5/2017 | Sanders |
| D793,553 | S | * | 8/2017 | Stillson ........................ D24/130 |
| 9,839,580 | B2 | | 12/2017 | Lev et al. |
| 9,855,191 | B1 | * | 1/2018 | Vitello ...................... A61J 1/18 |
| 9,884,177 | B2 | | 2/2018 | Ueda |
| 9,943,463 | B2 | | 4/2018 | Marks |
| 10,039,913 | B2 | | 8/2018 | Yeh et al. |
| 10,092,707 | B2 | | 10/2018 | Nguyen |
| 10,293,987 | B2 | | 5/2019 | Sattig |
| 10,300,263 | B1 | * | 5/2019 | Hunt .................. A61M 5/5086 |
| 10,391,031 | B2 | | 8/2019 | Yevmenenko |
| D862,694 | S | * | 10/2019 | Narvekar ..................... D24/130 |
| 10,543,150 | B2 | | 1/2020 | Noguchi |
| 10,569,014 | B2 | | 2/2020 | Hanson |
| 10,695,550 | B2 | | 6/2020 | Gardner |
| 10,773,068 | B2 | | 9/2020 | Yeh |
| 11,491,082 | B2 | * | 11/2022 | Nisler .................. A61J 1/1418 |
| 11,523,970 | B1 | * | 12/2022 | Vitello ................. A61J 1/1412 |
| 11,857,751 | B1 | * | 1/2024 | Vitello ............... A61M 5/5086 |
| 11,872,187 | B1 | * | 1/2024 | Vitello ............... A61M 5/5086 |
| 2001/0020607 | A1 | | 9/2001 | Chiarin |
| 2001/0048225 | A1 | | 12/2001 | Andre et al. |
| 2002/0125721 | A1 | | 9/2002 | Imaeda |
| 2002/0127150 | A1 | | 9/2002 | Sasso |
| 2002/0151851 | A1 | | 10/2002 | Fu |
| 2003/0070726 | A1 | | 4/2003 | Andreasson et al. |
| 2003/0075932 | A1 | | 4/2003 | Dolan |

(56)                    References Cited

U.S. PATENT DOCUMENTS

| | | | |
|---|---|---|---|
| 2003/0105434 A1 | 6/2003 | Chang | |
| 2003/0193190 A1* | 10/2003 | Werth | F16L 33/225 |
| | | | 285/243 |
| 2005/0209581 A1 | 9/2005 | Butts | |
| 2005/0258646 A1 | 11/2005 | Gunderson | |
| 2007/0060841 A1 | 3/2007 | Henshaw | |
| 2007/0250016 A1 | 10/2007 | Pech | |
| 2008/0172024 A1 | 7/2008 | Yow | |
| 2008/0269690 A1 | 10/2008 | Felix-Faure | |
| 2009/0177177 A1 | 7/2009 | Zinger | |
| 2010/0089862 A1 | 4/2010 | Schmitt | |
| 2010/0179506 A1 | 7/2010 | Shemesh | |
| 2010/0292673 A1 | 11/2010 | Korogi | |
| 2011/0054440 A1 | 3/2011 | Lewis | |
| 2011/0125128 A1 | 5/2011 | Nord | |
| 2012/0000881 A1 | 1/2012 | Sudo | |
| 2012/0220955 A1 | 8/2012 | Maseda | |
| 2012/0279968 A1 | 11/2012 | Levy Sarraf | |
| 2013/0030414 A1 | 1/2013 | Gardner et al. | |
| 2013/0092274 A1 | 4/2013 | Birch | |
| 2014/0021714 A1 | 1/2014 | Ueda | |
| 2014/0100533 A1* | 4/2014 | Lyons | A61M 39/20 |
| | | | 604/264 |
| 2014/0135738 A1 | 5/2014 | Panian | |
| 2015/0017363 A1 | 1/2015 | Buck | |
| 2015/0082746 A1 | 3/2015 | Ivosevic et al. | |
| 2015/0126974 A1 | 5/2015 | Sanders | |
| 2015/0265499 A1 | 9/2015 | Takeuchi | |
| 2015/0343154 A1 | 12/2015 | Liversidge | |
| 2015/0360826 A1 | 12/2015 | Fournier | |
| 2015/0366758 A1* | 12/2015 | Noguchi | A61J 1/2044 |
| | | | 604/407 |
| 2015/0367119 A1 | 12/2015 | Stillson | |
| 2016/0106929 A1 | 4/2016 | Fournier | |
| 2016/0206829 A1 | 7/2016 | Protasiewicz | |
| 2016/0250420 A1 | 9/2016 | Maritan | |
| 2017/0015476 A1 | 1/2017 | Mcclellan | |
| 2017/0028186 A1 | 2/2017 | Yeh | |
| 2017/0065486 A1 | 3/2017 | Mosler | |
| 2017/0165437 A1* | 6/2017 | Lopansri | A61M 5/002 |
| 2017/0189271 A1 | 7/2017 | Sanders | |
| 2017/0202742 A1 | 7/2017 | Cheng et al. | |
| 2017/0203091 A1 | 7/2017 | Sanders | |
| 2018/0064605 A1 | 3/2018 | Noguchi | |
| 2019/0111244 A1* | 4/2019 | Amon | A61M 39/12 |
| 2019/0282795 A1 | 9/2019 | Fangrow | |
| 2020/0397657 A1 | 12/2020 | Mio | |
| 2021/0038878 A1 | 2/2021 | Lofthouse | |
| 2021/0069419 A1* | 3/2021 | Pappalardo | A61M 5/31 |

FOREIGN PATENT DOCUMENTS

| | | |
|---|---|---|
| CN | 2933402 Y | 8/2007 |
| CN | 201101711 Y | 8/2008 |
| CN | 101626959 A | 1/2010 |
| CN | 201481796 U | 5/2010 |
| CN | 103068438 A | 4/2013 |
| CN | 103328339 A | 9/2013 |
| CN | 104364163 A | 2/2015 |
| CN | 104755059 A | 7/2015 |

| | | |
|---|---|---|
| CN | 206327707 | 7/2017 |
| JP | H04027760 U | 3/1992 |
| JP | 2006230739 | 9/2006 |
| JP | 2009529629 | 8/2009 |
| JP | 2010194237 A | 9/2010 |
| JP | 2011250851 A | 12/2011 |
| WO | WO-2012162259 | 11/2012 |
| WO | WO-2014033706 A2 | 6/2014 |

OTHER PUBLICATIONS

Australian Office Action for Application No. 2016297989, dated Jul. 21, 2020, 5 pages.
Australian Office Action for Application No. 2021203652, dated Nov. 11, 2021, 2 pages.
Canadian Office Action for Application No. 2994107, dated Aug. 29, 2023, 9 pages.
Canadian Office Action for Application No. 2994107, dated Nov. 3, 2022, 8 pages.
Chinese Office Action for Application No. 201610619274.8, dated Jul. 2, 2019, 12 pages.
Chinese Office Action for Application No. 201610619274.8, dated Feb. 1, 2019, 14 pages.
Chinese Office Action for Application No. 202010137455.3, dated Apr. 1, 2021, 10 pages including translation.
Chinese Office Action for Application No. 202010137455.3, dated Nov. 5, 2021, 14 pages including translation.
Chinese Office Action for Application No. 202010137455.3, Jul. 18, 2022, 16 pages including translation.
Chinese Office Action for Application No. 202211355783.6, dated Mar. 10, 2023, 6 pages including translation.
European Office Action for Application No. 19164049.9, dated May 24, 2023, 5 pages.
Extended European Search Report for Application No. 19164049.9, dated Mar. 19, 2020, 9 pages.
International Preliminary Report on Patentability from PCT/US2016/041616, dated Sep. 25, 2017, 11 pages.
International Search Report and Written Opinion for Application No. PCT/US2016/041616, dated Dec. 14, 2016, 17 pages.
Invitation to Pay Additional Fees and Partial International Search Report for Application No. PCT/US2016/041616, dated Oct. 20, 2016, 7 pages.
Japanese Office Action for Application No. 2018-504778, dated Jun. 24, 2020, 10 pages.
Japanese Office Action for Application No. 2021-155668, dated Apr. 4, 2023, 4 pages including translation.
Japanese Office Action for Application No. 2021-155668, dated Sep. 13, 2022, 6 pages including translation.
Australian Office Action for Application No. 2024200541, dated Dec. 24, 2024, 3 pages.
Chinese Office Action for Application No. 202211356405.X, dated Dec. 24, 2024, 20 pages including translation.
Canadian Office Action for Application No. 2,994,107, dated Oct. 2, 2024, 5 pages.
Japanese Office Action for Application No. 2023-142651, dated May 23, 2025, 4 pages including translation.
Chinese Decision of Rejection for Application No. 202211356405. X, dated Aug. 21, 2025, 8 pages including translation.

* cited by examiner

TAMPER-RESISTANT CAP

CROSS-REFERENCE TO RELATED APPLICATIONS

This application is a continuation of U.S. patent application Ser. No. 17/018,882, filed Sep. 11, 2020, entitled "TAMPER-RESISTANT CAP", which is a continuation of U.S. patent application Ser. No. 16/053,572, filed Aug. 2, 2018, entitled "TAMPER-RESISTANT CAP," now U.S. Pat. No. 10,773,068, which is a continuation of U.S. patent application Ser. No. 14/814,302, filed Jul. 30, 2015, entitled "TAMPER-RESISTANT CAP," now U.S. Pat. No. 10,039, 913, the disclosure of each of which is incorporated herein by reference in its entirety for all purposes.

BACKGROUND

The present disclosure relates generally to products, packages, or systems employing ports for conducting, for example, fluid through the product, package, or system. More particularly, the disclosure relates to tamper-proof caps for medical products, packages, or systems that have ports.

Products, packages, and systems used to retain and transmit medical fluids often comprise an access port for conducting fluid. For example, a port may be incorporated into an I.V. bag, a bottle, or a Y-site device installed along a fluid pathway. Through the port, a medical fluid may be introduced or withdrawn from the product, package, or system. Likewise, the port can present an opportunity for the medical fluid to become diluted, altered, or contaminated.

SUMMARY

Restricted access, through a port, to medical fluid is desired to prevent inadvertent contamination or spread of infection to the fluid. Unauthorized altering or adulteration is a serious threat to recipients of medical fluid that may change as a result of fluid infusion through the port. The unauthorized withdrawal of a portion of the medical fluid may also result in the recipient receiving an incorrect dosage of medical fluid. Additionally, toxic medical fluids, such as compounds used in chemotherapy, may be harmful to a person who comes into contact with the substance.

An aspect of the present disclosure provides a tamper-resistant cap for a medical adapter, the cap comprising: a housing having (i) an closed top end, (ii) an opposing open bottom end, and (iii) a side wall between the top end and the bottom end, the housing defining an axis extending between the top end and the bottom end; a plurality of legs that extend from the housing away from the bottom end; a member extending radially from an inner surface of at least one leg, wherein the member comprises a ramp surface, an engagement surface extending transversely to the ramp surface, and an apex area that transitions between the ramp surface and the engagement surface; wherein each leg is configured to flex radially in relation to the axis of the housing.

In some instances, a cross-sectional width between each radially-extending member is less than a cross-sectional width of an outer surface of a port. In some implementations, the legs combine to define an opening. In certain instances of the present disclosure, the housing comprises a first cross-sectional width at the bottom end that is greater than a second cross-sectional width at the top end. In some embodiments, an outer surface of the side wall is tapered from the bottom end to the top end. In some embodiments, an outer surface of the side wall comprises a plurality of ribs disposed from the bottom end to the top end.

In some embodiments of the present disclosure, a portion of each leg adjacent to the member defines a collar segment extending laterally from the leg. In some embodiments, each collar segment defines an arc. In some instances, each collar segment of the leg is configured to mate together to form a collar when the plurality of legs are pivoted toward the bottom end such that the collar is co-axial with the housing. In some implementations, each collar segment comprises one of at least a latch and a strike configured to couple each collar segment together. Some embodiments provide each leg is pivotable about a hinge. In some embodiments, the hinge is a living hinge.

An aspect of the present disclosure provides a tamper-resistant cap comprising: a housing having (i) an closed top end, (ii) an opposing open bottom end, and (iii) a side wall between the top end and the bottom end, the housing defining an axis extending between the top end and the bottom end; a plurality of legs that extend from the housing away from the bottom end, wherein the housing and at least one leg define at least one window; a tab extending from a bottom of each window toward the top end; and a member extending radially from an inner surface of each tab, wherein each member comprises a ramp surface, an engagement surface extending transversely to the ramp surface, and an apex area that transitions between the ramp surface and the engagement surface.

According to certain implementations of the present disclosure, the legs combine to define an opening. In some instances, a portion of the outer surface of the side wall is tapered toward the top end. In certain instances of the present disclosure, the housing comprises a first cross-sectional width at the bottom end that is greater than a second cross-sectional width at the top end.

Some embodiments provide an insert configured to mate within the housing between an inner surface of the top end and the engagement surface of each member, the insert comprising: a first end and an opposing second end, wherein the first end defines a cavity; wherein the inner surface of the top end and the second end are configured such that (i) the insert is configured to move a distance between the top end and each engagement surface, and (ii) the housing and insert engage to rotate together in one direction and disengage from each other when rotated in an opposite direction.

In some instances, an inner surface of the cavity comprises a thread. In some instances, the inner surface of the top end and the second end together comprise a ratchet and pawl. In some implementations, the cavity comprises a protrusion extending toward the first end. Some embodiments provide the first end further comprises a radial flange.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Figures 1, 2:
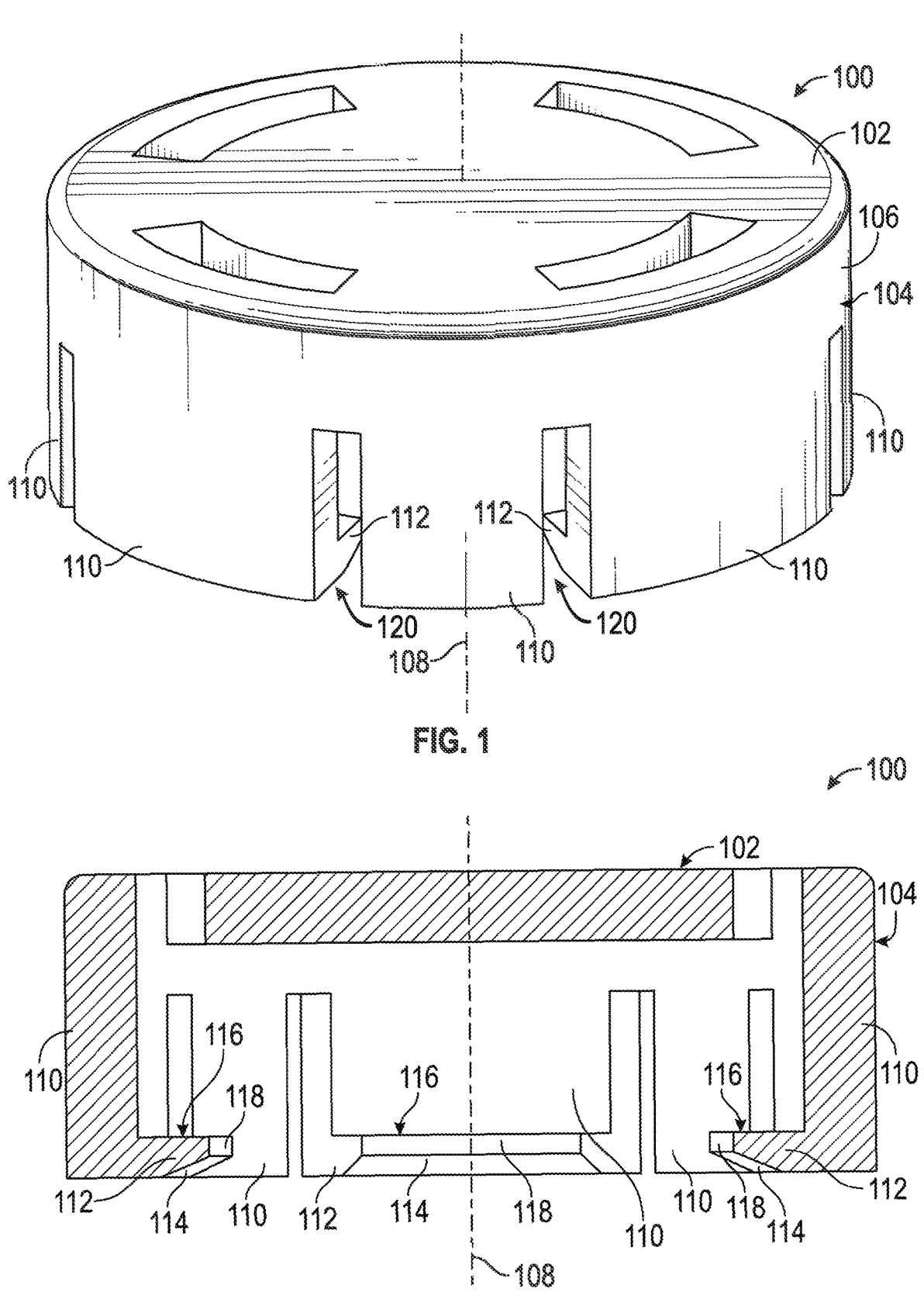
FIG. 1 illustrates a front perspective view of an embodiment of a tamper-resistant cap in accordance with aspects of the present disclosure.
FIG. 2 illustrates a sectional view of the tamper-resistant cap of FIG. 1.

The present disclosure relates to a tamper-resistant cap for use with products, packages, or systems employing an access port. FIG. 1 illustrates a tamper-resistant cap configured to be coupled to a port 900 having an exterior threads or a ridge 902. The tamper-resistant cap comprises a housing 100 having a closed top end 102 and an opposing open bottom end 104. A side wall 106 extends between the top end 102 and the bottom end 104, and is disposed circumferentially about an axis 108 extending between the top end 102 and the bottom end 104. In some embodiments, one or more apertures are disposed through the top end 102. A plurality of legs 110 extend from the housing 100 away from the bottom end 104, each leg 110 capable of flexing with respect to the axis 108. A space 120, defined between adjoining legs 110 and bounded at one end by the bottom end 104, allows each leg to flex independently of an adjoining leg 110. An inner surface of at least one leg 110 includes a member 112. Each member 112 extends radially inward from the inner surface of the leg 110 toward the axis 108.

Referring to FIG. 2, a plurality of legs 110 each comprise a member 112 extending toward the axis 108. Each member 112 comprises a ramp surface 114 and an engagement surface 116 extending toward the axis 108. The ramp surface 114 and the engagement surface 116 are oriented transversely to each other. An apex area 118 is disposed at the interface between the ramp surface 114 and the engagement surface 116. In a preferred embodiment, the cross-sectional width between the apex areas 118 of opposing radially-extending members 112 is less than the cross-sectional width of an exterior thread or ridge 902 of the port 904.

Figure 3:
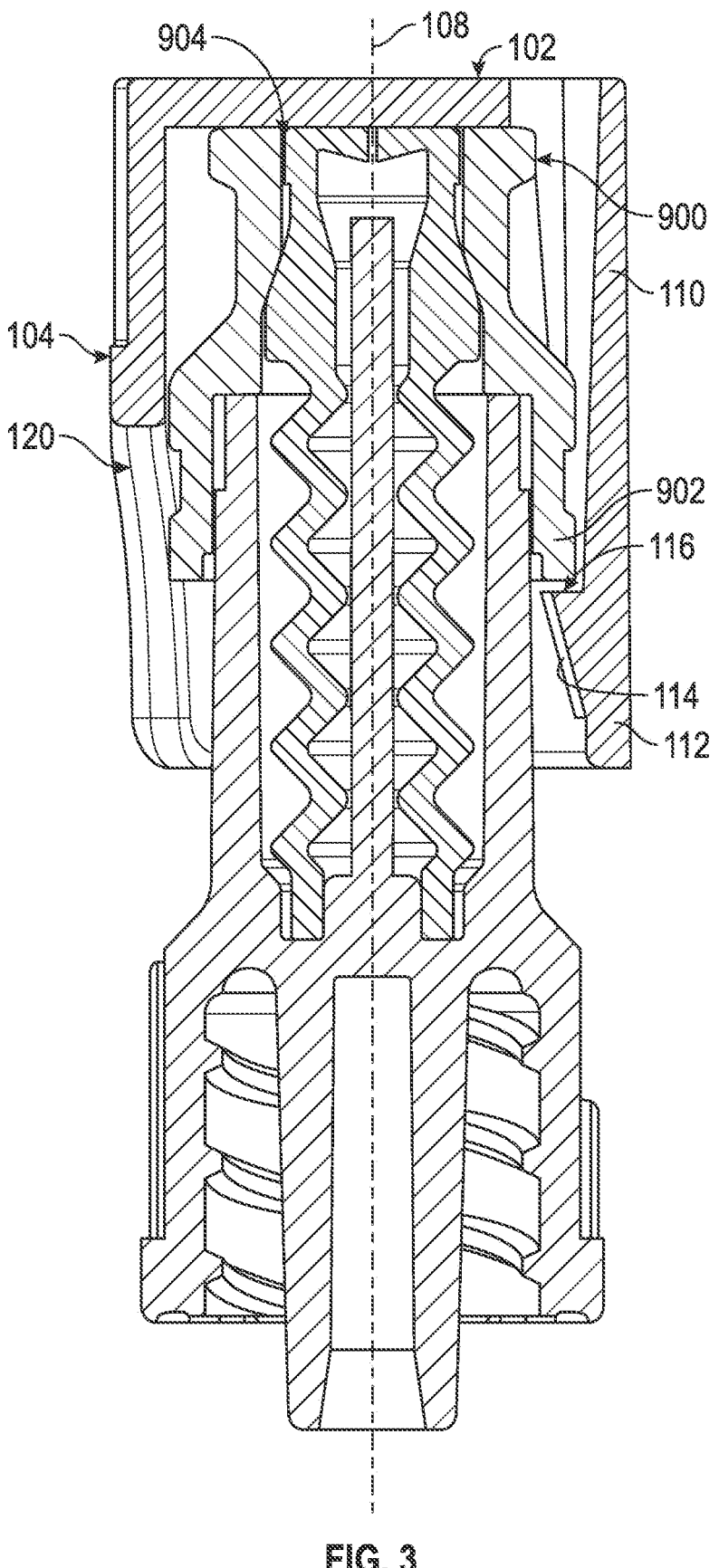
FIG. 3 illustrates a sectional view of an embodiment of a tamper-resistant cap coupled with a port in accordance with aspects of the present disclosure.

Referring to FIG. 3, the tamper-resistant cap may be coupled to a port 900 by first aligning the housing 100 with the port 900 such that the axis 108 is coaxial with the opening 904 of the port 900 and the legs 110 extend from the housing 100 toward the port 900. When the tamper-resistant cap is moved towards the port 900, the ramp surfaces 114 contact an exterior thread or ridge 902 on the port 900. As previously discussed with respect to FIG. 1, the space 120, defined between adjoining legs 110 and bounded at one end by the bottom end 104, allows each leg to flex independently of an adjoining leg 110. Additional movement of the tamper-resistant cap toward the port 900 causes the legs 110 to flex radially away from the axis 108. Once the legs 110 extend radially away from the axis 108, the tamper-resistant cap may be moved further onto the port 900 such that the apex area 118 passes over the exterior ridge or thread. After the apex area 118 passes over the exterior ridge or thread, the engagement surface 116 allows the legs to at least partially return toward the axis 108. In a preferred embodiment, the engagement surface 116 engages the exterior thread or ridge 902 of the port 900 but does not cause the legs to flex radially outward from the axis 108 when the tamper-resistant cap is moved in an opposite direct, away from the port 900.

Figure 4:
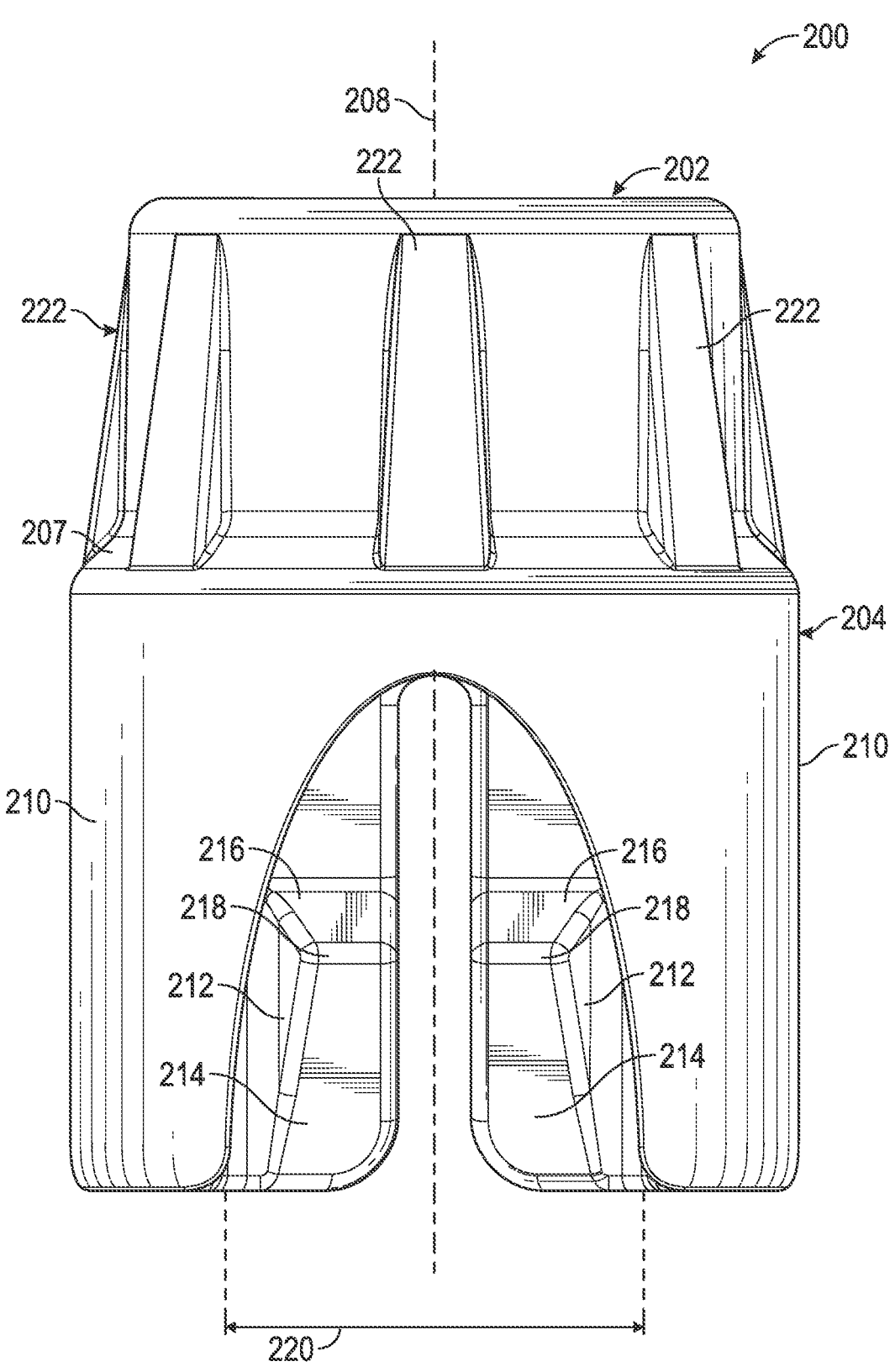
FIG. 4 illustrates a front view of an embodiment of a tamper-resistant cap in accordance with aspects of the present disclosure.
Figure 5:
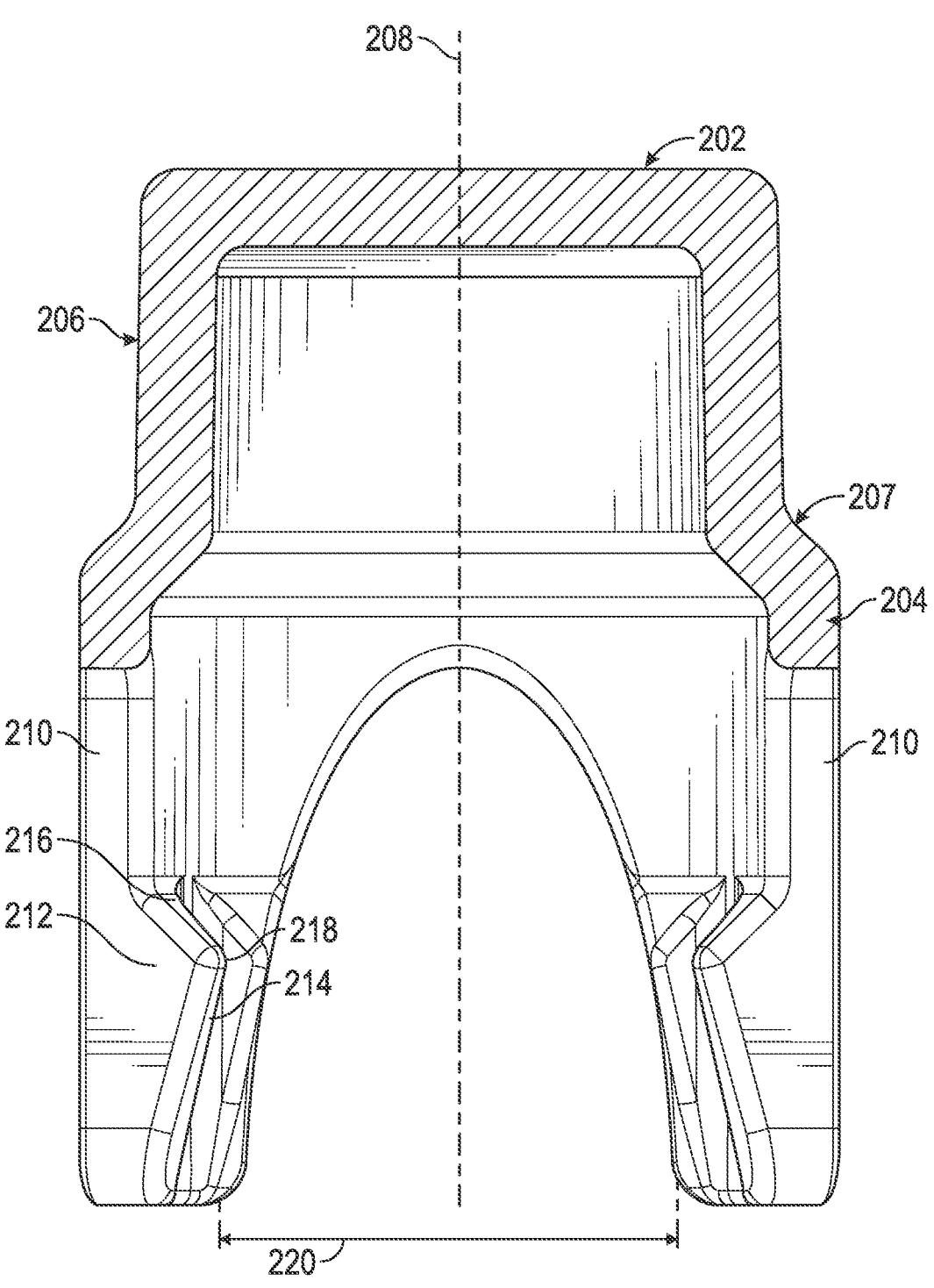
FIG. 5 illustrates a sectional view of the tamper-resistant cap of FIG. 4.

Referring to the embodiments of FIGS. 4-5, a tamper-resistant cap comprises a housing 200 having a closed top end 202, an opposing open bottom end 204, and a sidewall 206 extending between the top end 202 and bottom end 204. The sidewall 206 is disposed circumferentially about an axis 208 extending between the top end 202 and the bottom end 204. The exterior surface of the housing has a first cross-sectional width at the bottom end 204 and a second cross-sectional width at the top end 202. In a preferred embodiment, the first cross-sectional width is greater than the second cross-sectional width. In some embodiments, the exterior surface of the sidewall 206 includes a transition step 207 between the bottom end 204 and the top end 202. A plurality of ribs 222 are disposed on the sidewall 206 and extend from the bottom end 204 to the top end 202. The ribs 222 extend over the transition step 207 and are tapered from the first cross-sectional width at the bottom end 204 to the second cross-sectional width at the top end 202. In some embodiments, the exterior is sidewall 206 is tapered between the bottom end 204 the top end 202.

Referring to FIG. 5, a plurality of legs 210 extend from the housing 200 away from the bottom end 204. A member 212 is disposed on an inner surface of at least one leg 210. Each member 212 extends radially inward from the leg 210 toward the axis 208. Each member 212 comprises a ramp surface 214 and an engagement surface 216 extending toward the axis 208. An apex area 218 is disposed at the interface between the ramp surface 214 and the engagement surface 216. In a preferred embodiment, the cross-sectional width between the apex areas 216 of opposing radially-extending members 212 is less than the cross-sectional width of the exterior thread or ridge 902 of the port 900.

In some embodiments, the housing 200 and legs 210 define a space between each of the legs 210, thereby allowing each leg 210 to flex independently of the adjoining leg 210. In a preferred embodiment, the space defined by the housing 200 and legs 210 is an opening 220. The opening 220 allows the tamper-resistant cap to be coupled to a port on a device having an irregular area immediately adjacent to the port. For example, the opening 220 allows the tamper-resistant to be coupled to a Y-site (not shown) having a first branch and a second branch. When the tamper-resistant cap is coupled to a port on the first branch of a Y-site, the second branch extends through the opening 220.

Figure 6A:
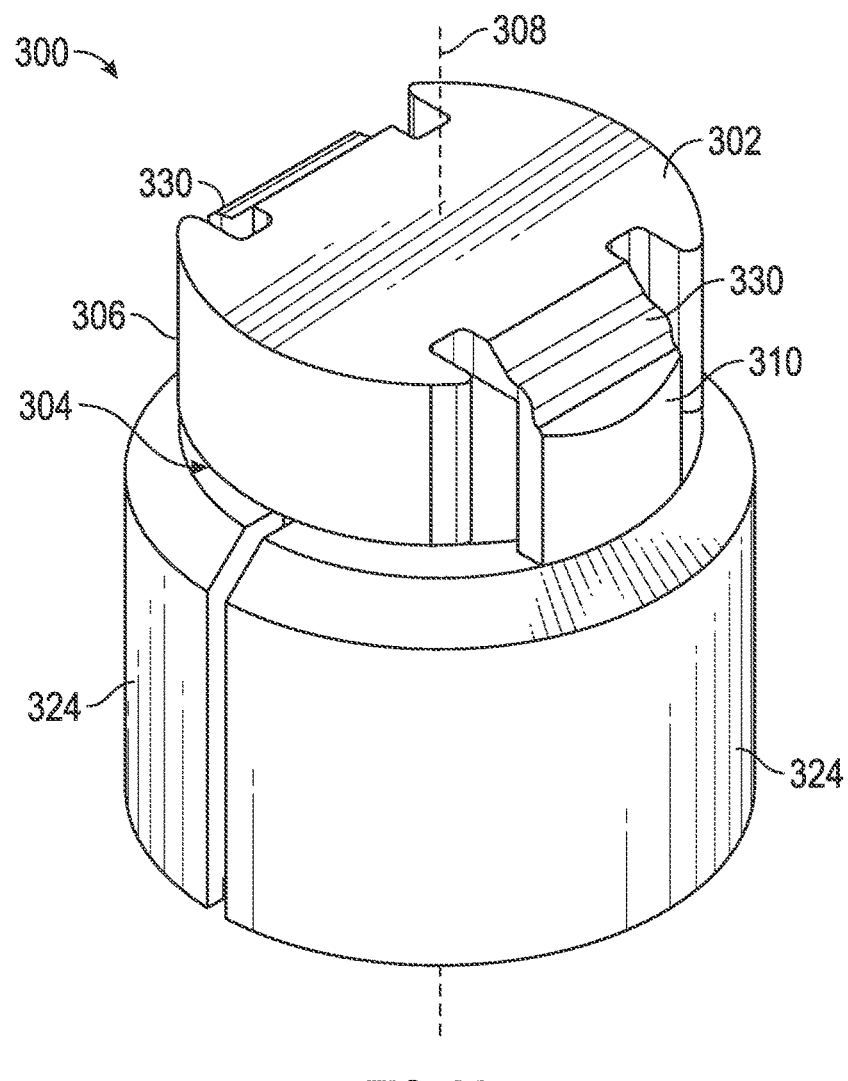
FIGS. 6A-6B illustrate front perspective views of an embodiment of a tamper-resistant cap in accordance with aspects of the present disclosure.
Figure 6B:
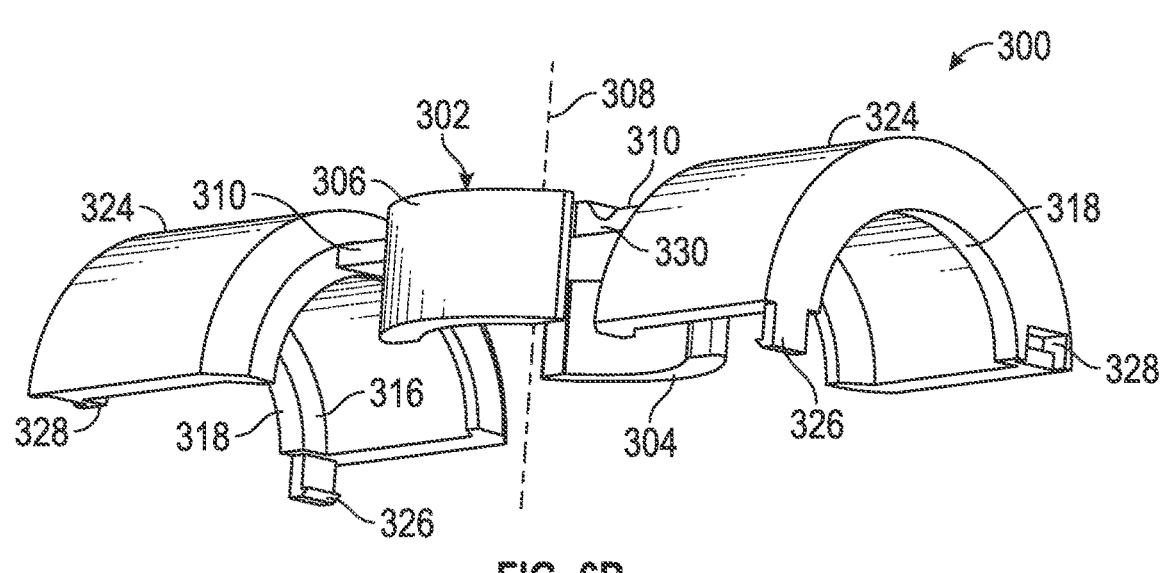
Figure 7:
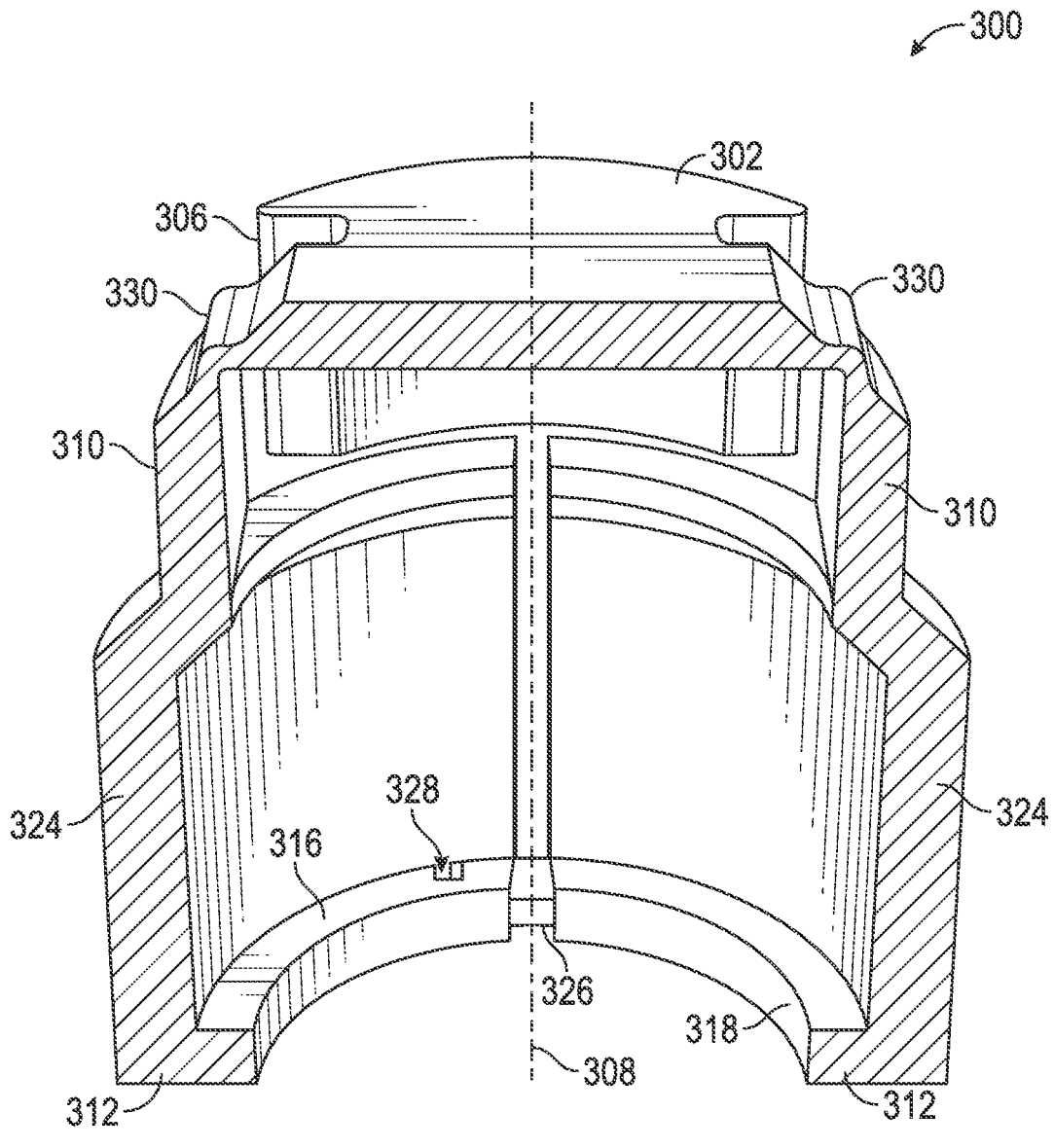
FIG. 7 illustrates a sectional view of the tamper-resistant cap of FIGS. 6A-6B.

FIGS. 6A-7 illustrate a tamper-resistant cap comprises a housing 300 having a closed top end 302, an opposing open bottom end 304, and a sidewall 306 extending between the top end 302 and bottom end 304. The sidewall 306 is disposed circumferentially about an axis 308 extending between the top end 302 and the bottom end 304.

A plurality of legs 310 extend from the top end 302 of the housing 300 toward the bottom end 304. Each leg is pivotably coupled at the top end 302 by a hinge 330. The hinge 330 allows each leg to pivot toward and away from the bottom end 304 along a plane parallel or substantially parallel to the axis 308, such that each leg can extend outward as depicted in FIG. 6B. In some embodiments, the hinge 330 is a thin flexible living hinge between each leg 310 and the top end 302.

A portion of each leg 310 adjacent to the member 312 defines a collar segment 324 extending laterally from the leg 310. Each collar segment 324 is shaped as an arc whereby a collar is formed when each leg 310 having a collar segment 324 is pivoted toward the axis 308. The collar portions 324 are configured to mate together to form a collar around the axis 308 of the housing 300. In some embodiments, the collar segments 324 mate together using a latch 326 and a strike 328 between each collar segment 324. In a preferred embodiment, a mating surface of each collar segment 324 comprises one of at least a latch 326 and a strike 328.

Referring to FIG. 7, a member 312 is disposed on an inner surface of each leg 310. Each member 312 extends radially inward from the leg 310 toward the axis 308. Each member 312 comprises an engagement surface 316 extending toward the axis 308, and an apex area 318. In a preferred embodiment, the cross-sectional width between the apex areas 318 of opposing radially-extending members 312 is less than the exterior thread or ridge 902 of the port 900.

The tamper-resistant cap of FIGS. 6A-7 can be coupled to a port 900 by first aligning the bottom end 304 of the housing 300 with the port 900 such that the axis 308 is coaxial with the opening 904 of the port 900. The legs 310 may then be pivoted toward the bottom end 304 until a collar segment 324 is adjacent to an outer surface of the port 900, and the engagement surface 316 is adjacent to an exterior thread or ridge 902 of the port 900. Each collar segment 324 may then be coupled together by engaging each latch 326 and strike 328 combination. Once the collar segments are 324 are engaged, the engagement surface 316 abuts the exterior thread or ridge 902 of the port 900 but does not cause the legs to flex away from the axis 308 when the tamper-resistant cap is moved in an opposite direct, away from the port 900.

Figure 8:
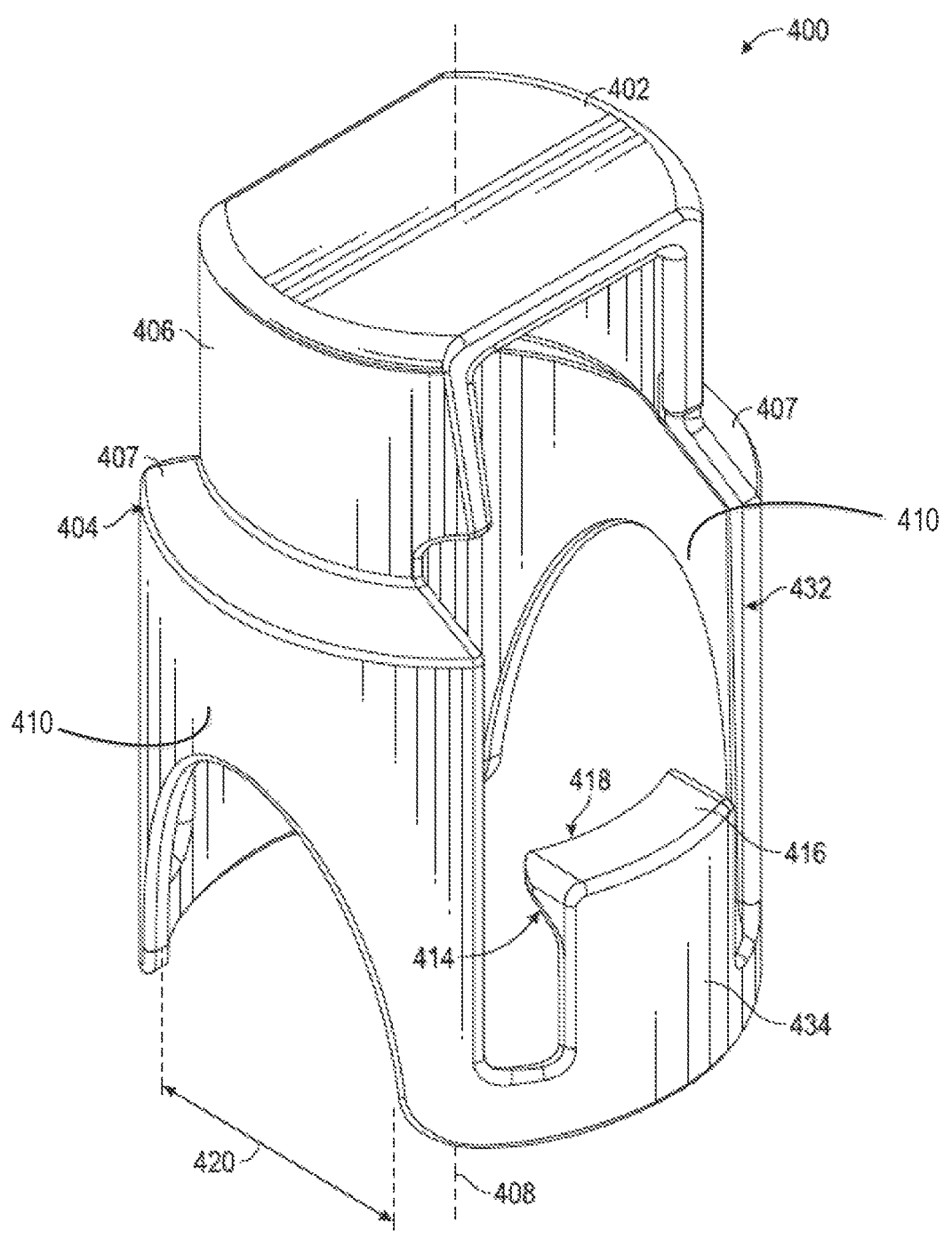
FIG. 8 illustrates a front perspective view of an embodiment of a tamper-resistant cap in accordance with aspects of the present disclosure.
Figure 9:
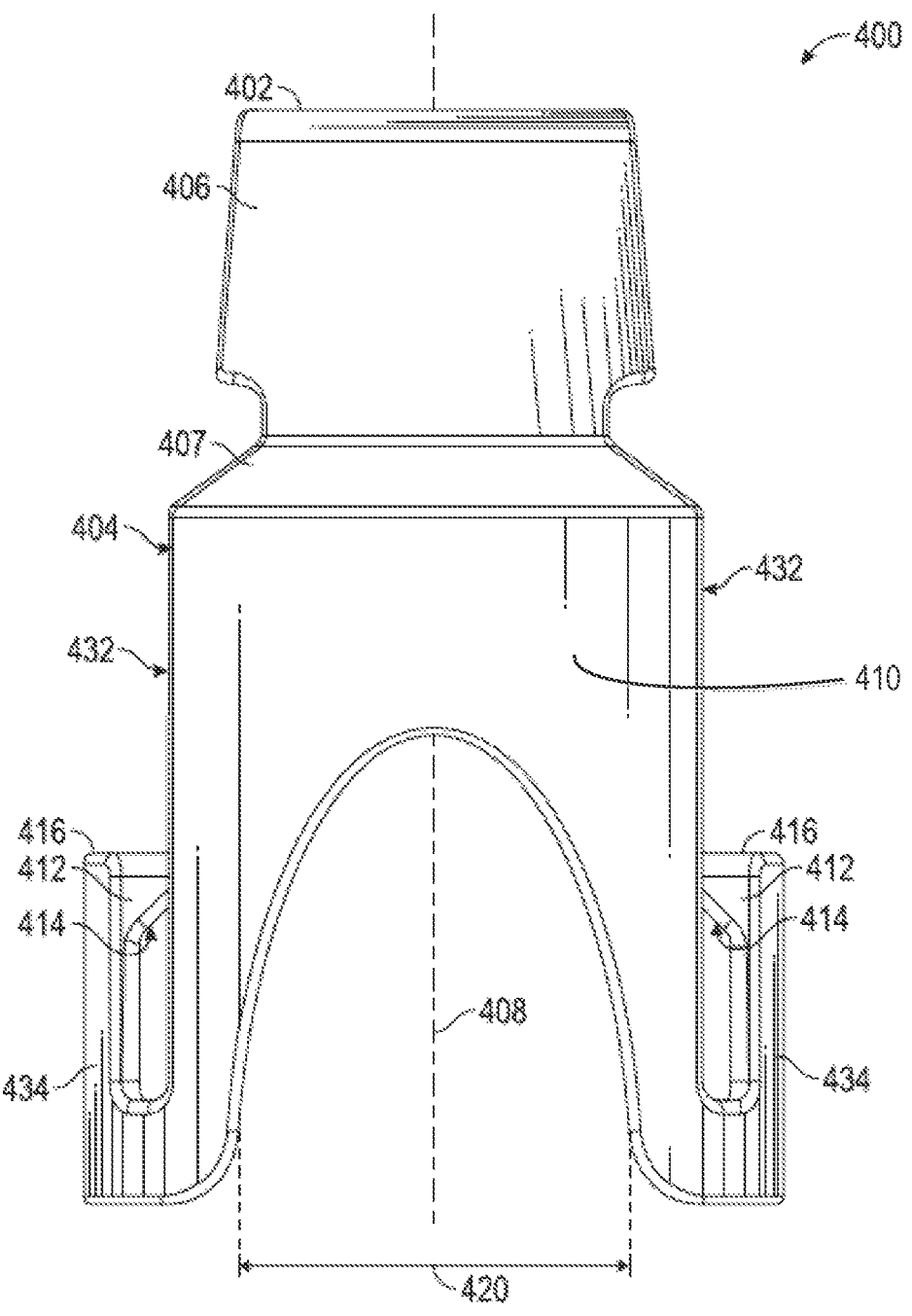
FIG. 9 illustrates a front view of the tamper-resistant cap of FIG. 8.
Figure 10:
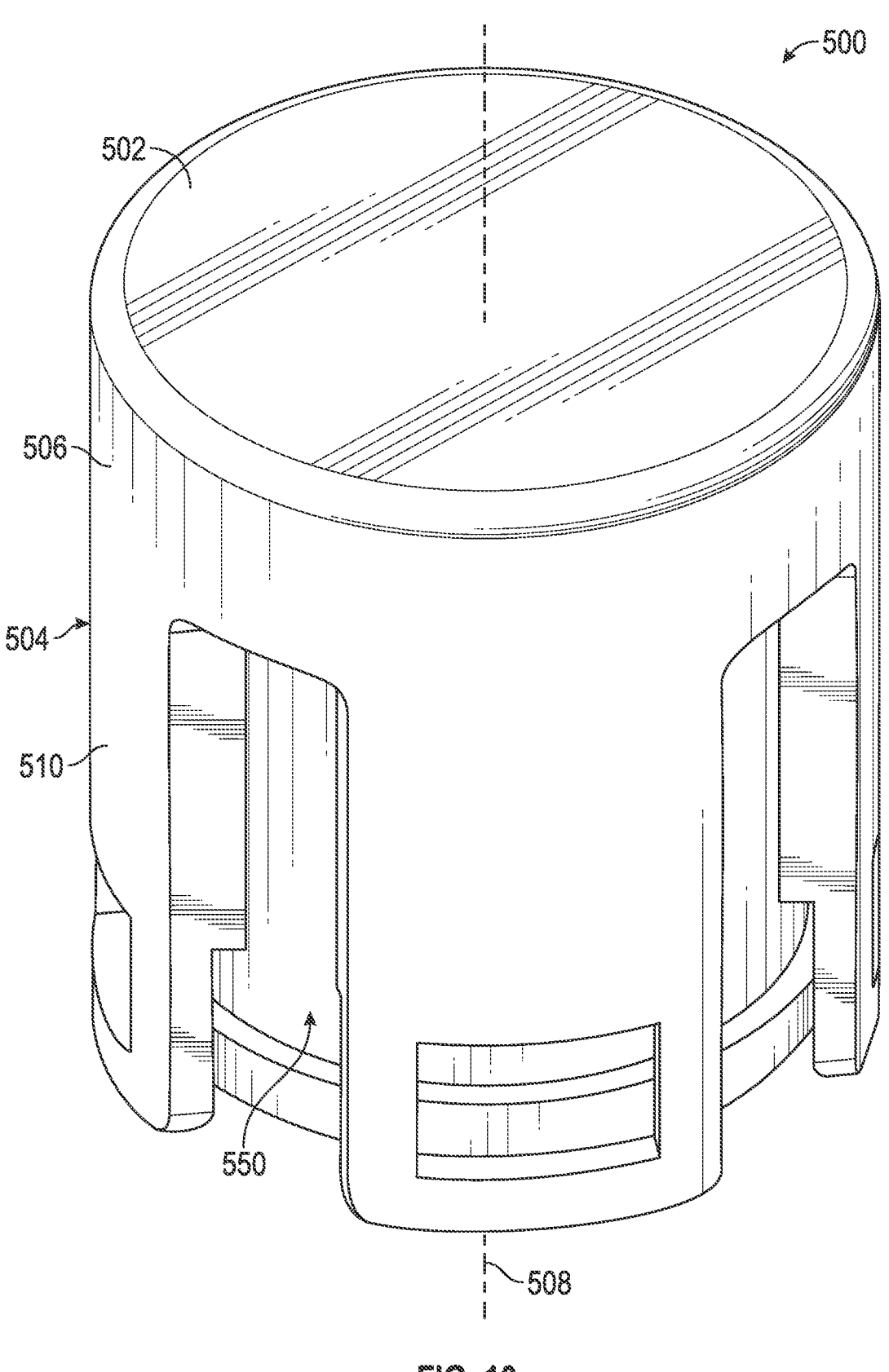
FIG. 10 illustrates a front perspective view of an embodiment of a tamper-resistant cap in accordance with aspects of the present disclosure.

Referring to FIGS. 8-9, a tamper-resistant cap comprises a housing 400 having a closed top end 402, an opposing open bottom end 404, and a sidewall 406 extending between the top end 402 and bottom end 404. The sidewall 406 is disposed circumferentially about an axis 408 extending between the top end 402 and the bottom end 404. The exterior surface of the housing has a first cross-sectional width at the bottom end 404 and a second cross-sectional width at the top end 402. In a preferred embodiment, the first cross-sectional width is greater than the second cross-sectional width. In some embodiments, a portion of the exterior surface of the sidewall 406, between the first cross-sectional width at the bottom end 404 and the second cross-sectional width at the top end 402, includes a transition step 407.

A plurality of legs 410 extend from the housing 400 away from the bottom end 404. In some embodiments, a window 432 is defined by the housing 400 and at least one leg 410. A tab 434 extends from an edge of each window, towards the top end 402. Preferably, the tab 434 extends from an edge of the window opposite the top end 402. A member 412 is disposed on an inner surface of each tab 434. Each member 412 extends radially inward from the tab 434 toward the axis 408. Each member 412 comprises a ramp surface 414 and an engagement surface 416 extending toward the axis 408. An apex area 418 is disposed at the interface between the ramp surface 414 and the engagement surface 416. In a preferred embodiment, the cross-sectional width between the apex areas 418 of opposing radially-extending members 412 is less than the cross-sectional width of the exterior thread or ridge 902 of the port 900.

In some embodiments, an opening 420 is defined by the housing 400 and legs 410 between each of the legs 410. The opening 420 allows the tamper-resistant cap to be coupled to a port on a device having an irregular area immediately adjacent to the port. For example, the opening 420 allows the tamper-resistant to be coupled to a Y-site (not shown) having a first branch and a second branch. When the tamper-resistant cap is coupled to a port on the first branch of a Y-site, the second branch extends through the opening 420.

In some embodiments, a plurality of ribs are disposed on the sidewall 406 and extend from the bottom end 404 to the top end 402. The ribs extend over the transition step 407 and are tapered from the first cross-sectional width at the bottom end 404 to the second cross-sectional width at the top end 402. In some embodiments, the exterior sidewall 406 is tapered between the bottom end 404 the top end 402.

The tamper-resistant cap may be coupled to a port 900 by first aligning the housing 400 with the port 900 such that the axis 408 is aligned and coaxial with the opening 904 of the port 900 and the legs 410 extending from the housing 400 toward the port 900. When the tamper-resistant cap is moved towards the port 900, the ramp surfaces 414 contact an exterior thread or ridge 902 on the port 900. Additional movement of the tamper-resistant cap toward the exterior thread or ridge 902 causes the tabs 434 to flex radially away from the axis 408. Once the tabs 434 extend radially away from the axis 408, the tamper-resistant cap may be moved further onto the port 900 such that the apex area under 418 passes over the exterior thread or ridge 902. After the apex area 418 passes over the exterior ridge or thread, the engagement surface 416 allows the legs to at least partially return toward the axis 408. In a preferred embodiment, the engagement surface 416 engages the exterior thread or ridge 902 of the port 900 but does not cause the legs to flex radially outward from the axis 408 when the tamper-resistant cap is moved in an opposite direct, away from the port 900.

FIGS. 10-13 illustrate a tamper-resistant cap comprising a housing 500 and an insert 550. The housing 500 has a closed top end 502, an opposing open bottom end 504, and a sidewall 506 extending between the top end 502 and bottom end 504. The sidewall 506 is disposed circumferentially about an axis 508 extending between the top end 502 and the bottom end 504. A plurality of legs 510 extend from the housing 500 away from the bottom end 504.

Figure 11:
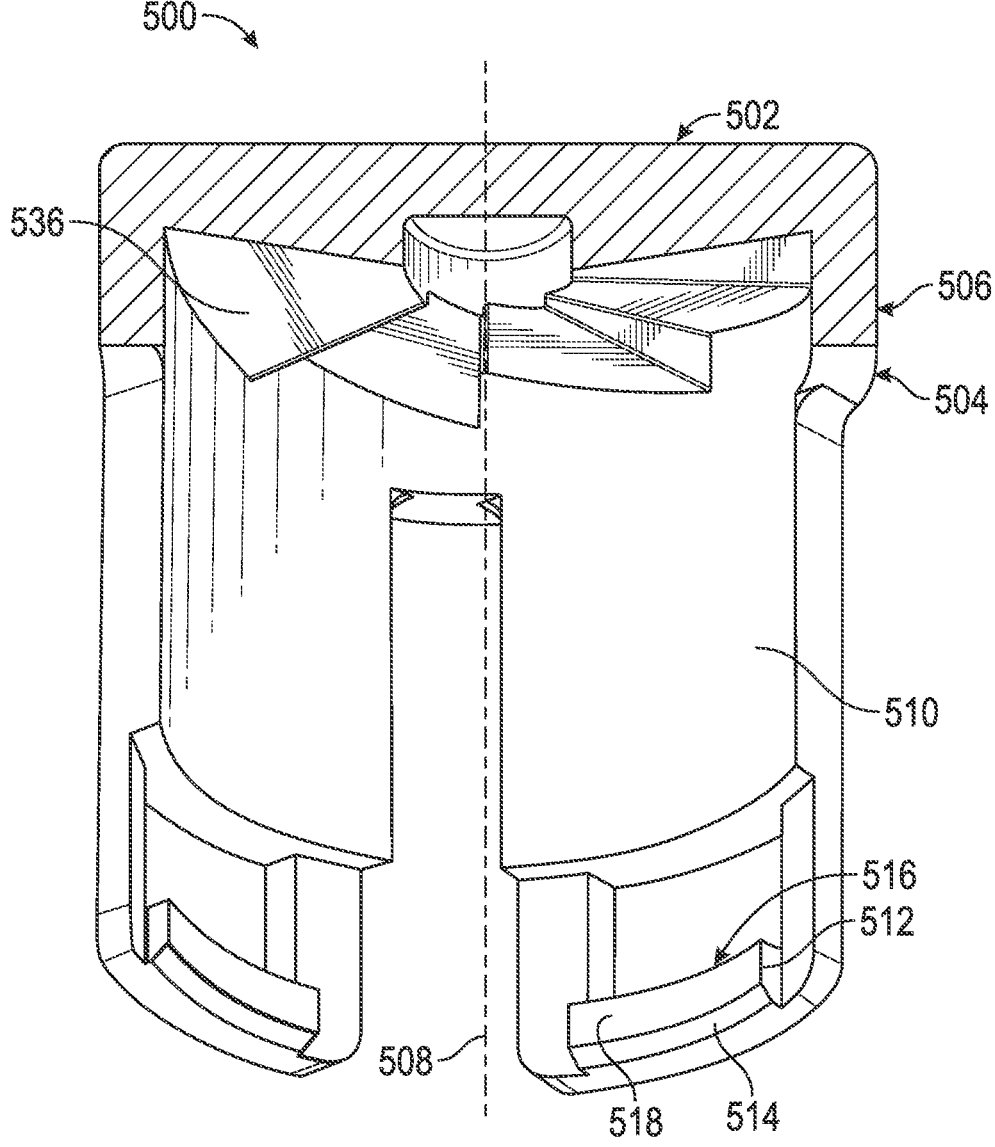
FIG. 11 illustrates a sectional view of a housing for the tamper-resistant cap of FIG. 10.

Referring to FIG. 11, the housing 500 and legs 510 define a space between each of the legs 510, thereby allowing each leg 510 to flex independently of the adjoining leg 510. A member 512 is disposed on an inner surface of each leg 510. Each member 512 extends radially inward from the leg 510 toward the axis 508. Each member 512 comprises a ramp surface 514 and an engagement surface 516 extending toward the axis 508. An apex area 518 is disposed at the interface between the ramp surface 514 and the engagement surface 516. The inside surface of the top end 502 of the housing 500 comprises a circumferential series of angular ridges 536.

Figure 12:
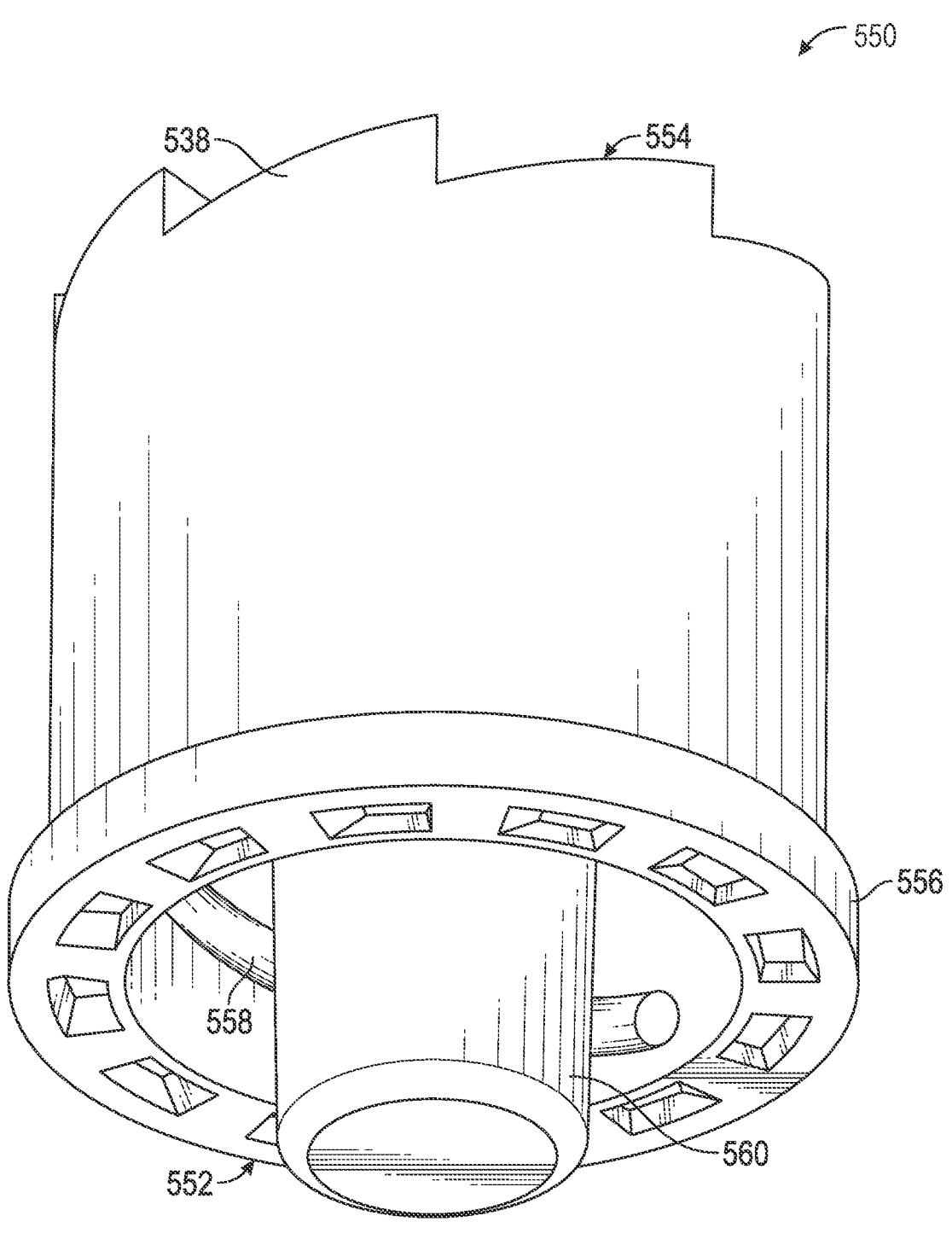
FIG. 12 illustrates a front perspective view of an insert for the tamper-resistant cap of FIG. 10.

FIG. 12 illustrates an insert 550 having a first end 552 and an opposing second end 554. The insert 550 defines a flange 556, disposed at the first end 552 and extending radially away from the insert 550. In a preferred embodiment, the cross-sectional width between the apex areas 518 of opposing members 512 is less than the cross-sectional width of the flange 556.

The insert 550 further defines a cavity through the first end 552 extending partially toward the inside surface of the second end 554. In some embodiments, an inside surface of the cavity comprises a threaded surface 558. In some embodiments, a protrusion 560 extends from the inside surface of the second end 554 toward the first end 552. In a preferred embodiment, the protrusion 560 extends past a plane defined by the first end 552. The outside surface of the second end 552 comprises a circumferential series of angular ridges 538. The angular ridges 538 of the second end 552 are oriented in an opposite direction to the angular ridges 536 of the top end 502.

Figure 13:
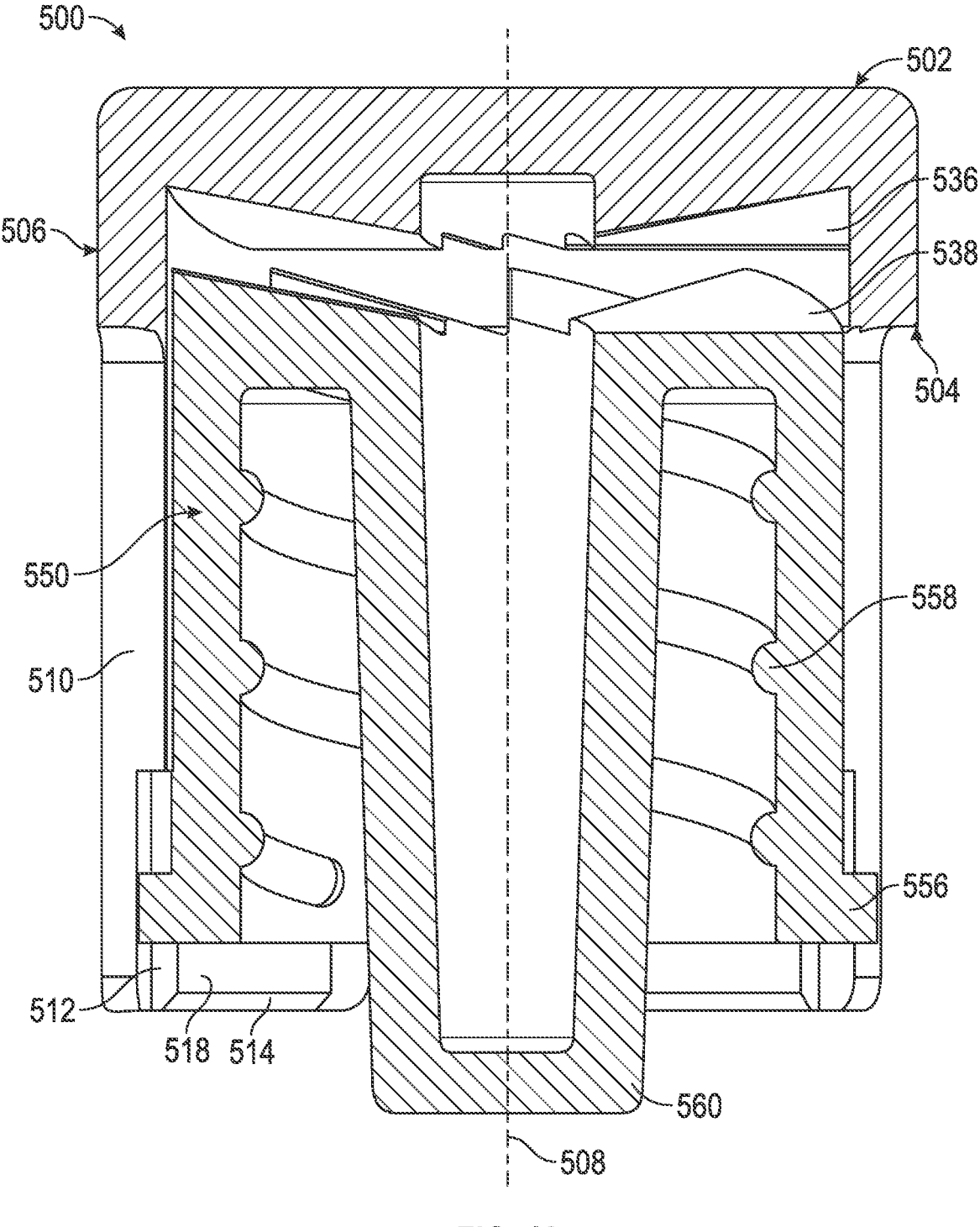
FIG. 13 illustrates a sectional view of the tamper-resistant cap of FIG. 10.

Referring to FIG. 13, the housing 500 and insert 550 are coupled together by aligning the legs 510 of housing 500 with the second end 554 of the insert 550. When the housing 500 is moved towards and over the insert 550, the ramp surfaces 514 contact the flange 556 and cause the legs 510 to flex radially away from the axis 508. Once the legs 510 extend radially away from the axis 508, the housing 500 may be moved further over the insert 550 such that the apex area 518 passes over the flange 556, allowing the legs 510 to at least partially return toward the axis 508. The insert 550 is retained within the legs 510 of the housing 500, between the inside surface of the top end 502 and the engagement surface 516.

Because the distance between the first end 552 and the second end 554 of the insert 550 is less than the distance between the inside surface of the top end 502 and the engagement surface 516, the insert 550 can move a distance between the inside surface of the top end 502 and the engagement surface 516.

When the top end 502 of the housing 500 is moved toward the second end 554 of the insert 550, the angular ridges 536 of the housing 500 engage with the angular ridges 538 of the insert 550 thereby allowing the housing 500 and insert 550 to rotate together in a first direction. When the housing 500 is moved away from the second end 554, or the rotated in a second, opposite direction, the angular ridges 536 of the housing 500 disengage from the angular ridges 538 of the insert 550. In some embodiments, the tamper-resistant cap is coupled to a port 900 by first affixing the insert 550 to the port 900. In a preferred embodiment, the insert 550 is coupled to the port 900 using the threads 558 such that the protrusion 560 extends into the port 900. Next, the housing 500 is coupled to the insert 550, whereby the combined housing 500 and insert 550 may engage to rotate in a first direction, but disengage when turned in a second, opposite, direction. In some embodiments, the housing 500 and insert 550 are first coupled together. Next, the threads 558 of the insert 550 are aligned with a port 900. The housing 500 is then moved towards the insert 550 such that the angular ridges 536 and 538 engage each other and allow the housing 500 and insert 550 to be rotated in a first direction, thereby coupling the housing 500 and insert 550 to the port 900.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A tamper-resistant cap for a medical adapter, the tamper-resistant cap comprising:

a housing having a closed top end, an open bottom end opposite to the closed top end, and a side wall between the top end and the bottom end, the housing defining an axis extending between the top end and the bottom end; and a plurality of legs extending from the housing in a direction toward the bottom end, wherein each leg of the plurality of legs intersects the side wall and is pivotably coupled to the top end, and each leg of the plurality of legs comprises a collar segment;

wherein the collar segment of each leg of the plurality of legs is configured to mate together to form a collar when the plurality of legs are pivoted toward the axis.

2. The tamper-resistant cap of claim 1, wherein the collar segment of each leg of the plurality of legs extends laterally from the respective leg of the plurality of legs.

3. The tamper-resistant cap of claim 2, wherein the collar segment of each leg of the plurality of legs defines an arc.

4. The tamper-resistant cap of claim 1, wherein the collar segment of each leg of the plurality of legs comprises a member extending radially inward from an inner surface of the collar.

5. The tamper-resistant cap of claim 1, wherein each collar segment of each leg of the plurality of legs comprises one of at least a latch and a strike configured to couple each collar segment together.

6. The tamper-resistant cap of claim 1, wherein each leg is pivotable about a hinge.

7. The tamper-resistant cap of claim 6, wherein the hinge is a living hinge.

* * * * *